United States Patent
Hartley et al.

(10) Patent No.: US 8,597,346 B2
(45) Date of Patent: Dec. 3, 2013

(54) STENT GRAFTS FOR THE THORACIC AORTA

(71) Applicants: Cook Medical Technologies LLC, Bloomington, IN (US); William A. Cook Pty. Ltd., Brisbane (AU)

(72) Inventors: David Ernest Hartley, Wannanup (AU); Werner Dieter Ducke, Queensland (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/764,092

(22) Filed: Feb. 11, 2013

(65) Prior Publication Data

US 2013/0150944 A1   Jun. 13, 2013

Related U.S. Application Data (62) Division of application No. 12/152,057, filed on May 12, 2008, now Pat. No. 8,377,113.

(60) Provisional application No. 60/928,731, filed on May 11, 2007.

(51) Int. Cl.
   *A61F 2/06*         (2013.01)

(52) U.S. Cl.
   USPC ............................................. 623/1.23

(58) Field of Classification Search
   USPC .............. 623/1.11, 1.12, 1.13, 1.23; 606/108, 606/191, 194, 198, 200
   See application file for complete search history.

(56) References Cited

U.S. PATENT DOCUMENTS

| 6,471,722 B1 | 10/2002 | Inoue ............................ 623/1.35 |
| 6,485,515 B2 | 11/2002 | Strecker ........................ 623/6.12 |

(Continued)

FOREIGN PATENT DOCUMENTS

| JP | 03133446 A | 6/1991 |
| JP | 2005000569 A | 1/2005 |

(Continued)

OTHER PUBLICATIONS

International Search Report and Written Opinion for PCT/US2008/006025 dated Jul. 28, 2008 (9 pages).

(Continued)

*Primary Examiner* — Ryan Severson
*Assistant Examiner* — Katherine M Shi
(74) *Attorney, Agent, or Firm* — Brinks Gilson & Lione (57) ABSTRACT

A method of temporarily reducing the diameter of a stent graft (10) and a stent graft with its diameter reduced. The stent graft has a tubular body and self expanding stents. The method comprising extending a release wire (18, 20) part helically along the graft material tube from substantially one side of the graft material tube at one end (14) of the graft material tube to substantially the opposite side of the graft material tube at the other end (12) of the graft material tube along the stent graft and stitching the release wire into the graft material tube, at each of a number of positions along the release wire looping flexible threads (22, 24) around the release wire and extending the flexible threads laterally around the circumference of the stent graft in each direction to a position away from the release wire, engaging the first flexible threads into the graft material or around struts of the stent, and drawing the ends of the thread together and tying ends of the thread to thereby temporarily reduce the overall diameter of the stent graft.

7 Claims, 5 Drawing Sheets

(56) References Cited

U.S. PATENT DOCUMENTS

| | | | | |
|---|---|---|---|---|
| 6,524,335 | B1 | 2/2003 | Hartley et al. | 623/1.13 |
| 6,716,238 | B2 | 4/2004 | Elliott | 623/1.11 |
| 2005/0049674 | A1 | 3/2005 | Berra et al. | 623/1.13 |
| 2005/0060018 | A1 | 3/2005 | Dittman | 623/1.11 |

FOREIGN PATENT DOCUMENTS

| | | |
|---|---|---|
| JP | 2005058459 A | 3/2005 |
| WO | WO 03/101518 A1 | 12/2003 |
| WO | WO 2006/007389 A1 | 1/2006 |
| WO | WO 2007/022495 A1 | 2/2007 |

OTHER PUBLICATIONS

Office Action received for related U.S. Appl. No. 12/152,057 dated May 26, 2010 (17 pages).
Office Action received for related U.S. Appl. No. 12/152,057 dated Sep. 28, 2010 (12 pages).
Advisory Action received for related U.S. Appl. No. 12/152,057 dated Dec. 7, 2010 (4 pages).
Advisory Action received for related U.S. Appl. No. 12/152,057 dated Dec. 30, 2010 (3 pages).
Office Action received for related U.S. Appl. No. 12/152,057 dated Nov. 22, 2011 (10 pages).
Office Action received for related U.S. Appl. No. 12/152,057 dated Apr. 11, 2012 (11 pages).
Pre-Brief Appeal Conference Decision received for related U.S. Appl. No. 12/152,057 dated Oct. 1, 2012 (3 pages).

STENT GRAFTS FOR THE THORACIC AORTA

CROSS-REFERENCE TO RELATED APPLICATIONS

This application is a divisional application of nonprovisional application Ser. No. 12/152,057 filed May 12, 2008 which claims priority to provisional application Ser. No. 60/928,731, filed May 11, 2007.

TECHNICAL FIELD

This invention relates to a medical device and more particularly to a stent graft for mounting onto a deployment device for endovascular introduction.

BACKGROUND OF THE INVENTION

This invention will be particularly discussed in relation to stent grafts for placement into the thoracoabdominal aorta for the treatment of aneurysms and more specifically in relation to placement in a curved portion of the aorta such as the thoracic arch. The invention, however, is not so restricted and may be applied to stent grafts for placement in any lumen of the human or animal body.

A stent graft particularly for the thoracic arch may have one or more fenestrations or a scallop at the proximal end to prevent occlusion of one or more of the major arteries which extend from the thoracic arch. A stent graft is in a constricted form when it is delivered by endoluminal techniques to a deployment site within such a curved lumen and in that condition it is difficult for a physician to determine whether the fenestrations or scallop are correctly aligned to be positioned upon release by withdrawal of a covering sheath. There have been devised diameter reducing arrangements for stent grafts so that there is a partial release stage of the stent graft after the covering sheath has been withdrawn. At this stage the stent graft has expanded in diameter to such an extent that the physician can visualise using radiographic techniques the position of the fenestrations or scallop while at the same time the stent graft can still be rotated and move longitudinally to position the fenestrations or scallop correctly. The diameter reducing arrangements can be subsequently released to allow the stent graft to fully expand engage the wall of the vessel to form an alternative flow path through the vessel to bypass an aneurysm, for instance.

The problem with a curved lumen with significant continuing blood flow and such a staged release arrangement is that the proximal or leading edge of the stent graft particularly at the inner side of the curved lumen may not engage against the wall of the lumen and may fold in thereby blocking the desired flow path and allowing bypass to continue into the aneurysm.

It is an object of this invention to provide a diameter reducing arrangement so that this problem can be reduced or to at least to provide a physician with an alternative arrangement.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

In one form therefore the invention is said to reside in a temporary diameter reduction constraint arrangement for a stent graft, the stent graft comprising a biocompatible graft material tube of a selected diameter and having a first end and a second end and a plurality of self expanding stents fastened thereto, the constraint arrangement comprising at least one release wire extending part helically along the graft material tube from substantially one side of the graft material tube at the first end of the graft material tube to substantially the opposite side of the graft material tube at the second end of the graft material tube and a plurality of circumferential threads spaced apart at positions along the graft material tube and engaged around the release wire and a portion of the stent graft circumferentially spaced a selected distance away from the release wire and drawn tight and tied to reduce the circumference and hence the overall diameter of the stent graft.

The stent graft can be mounted onto a deployment device such that at the proximal end of the stent graft the diameter reducing ties are at the inner side of what would be the curve of the deployment device to fit the curved lumen and at the distal end they are on the outer side of the curved lumen. This has a number of advantages. A first is that upon partial release the outer side of the curve at the proximal end expands more fully while at the same time still being maneuverable which allows the fenestration or scallops to be more opened and hence easier to visualise and position correctly. A second advantage is that when the diameter reducing ties are released by withdrawing the release wire there is a certain degree of friction between the release wire and the graft material through which it is stitched and pulling the release wire actually pulls the inner curve side of the proximal end of the stent graft towards the inner curve of the lumen thereby assisting the inner curve side of the proximal end of the stent graft to correctly engage with the wall of the lumen. A third advantage is that when the stent graft is in its curved and partially released configuration the release wire is substantially straighter between the ends of the graft thereby reducing the chance that the release wire will buckle and be difficult to withdraw when required.

Preferably the circumferential thread extends circumferentially in each direction from the release wire at each of the positions.

In a preferred embodiment the stents are zig-zag stents comprising struts and bends therebetween and the engagement of the flexible thread into the graft material includes the engagement of the thread around a strut of the self expanding stent.

The selected distance may be reduced by from 50 to 75%.

In a preferred embodiment there may be two release wires and a circumferential thread extending circumferentially in each direction from each of the release wires at the plurality of positions along the release wires to hold the stent graft at a reduced diameter along the length of the stent graft. The two release wires may extend from substantially the corresponding circumferential position at one end of the stent graft helically in opposite directions to substantially the corresponding circumferential position at the other end of the stent graft.

In an alternative form the invention comprises a method of temporarily reducing the diameter of a stent graft at a plurality of positions along the stent graft, the stent graft comprising a tubular body of a biocompatible graft material and having a first end and a second end and a plurality of self expanding stents, the method comprising the steps of;

a) extending a release wire part helically along the graft material tube from substantially one side of the graft material tube at the first end of the graft material tube to substantially the opposite side of the graft material tube at the second end of the graft material tube along the stent graft and stitching the release wire into the graft material tube;

b) at each of a plurality of positions along the release wire looping a first flexible thread around the release wire and extending the first flexible thread laterally around the circumference of the stent graft to a position a selected distance from the release wire;

c) engaging the first flexible thread into the graft material and/or a stent strut, and d) drawing the ends of the thread together and tying ends of the thread, whereby the selected distance is reduced thereby temporarily reducing the overall diameter of the stent graft.

The method can further comprise the steps of;

e) passing a second flexible thread around the release wire or the first flexible thread and extending the second flexible thread laterally around the circumference of the stent graft in the opposite direction to the first flexible thread to a position a selected distance from the release wire at each of the plurality positions along the length of the release wire;

f) engaging the second flexible thread into the graft material and/or a stent strut, and g) drawing the ends of the second thread together and tying ends of the thread, whereby the selected distance is reduced thereby reducing the overall diameter of the stent graft.

The method can further comprise the steps of;

j) extending a second release wire along the stent graft on an opposite side of the graft material tube from substantially one side of the graft material tube at the first end of the graft material tube to substantially the opposite side of the graft material tube at the second end of the graft material tube along the stent graft and stitching the release wire into the graft material tube;

k) looping a third flexible thread around the second release wire and extending the third flexible thread laterally around the circumference of the stent graft to a position a selected distance from the second release wire;

l) engaging the third flexible thread into the graft material and/or a stent strut, and m) drawing the ends of the thread together and tying ends of the thread, n) passing a fourth flexible thread around the release wire or around the third flexible thread and extending the fourth flexible thread laterally around the circumference of the stent graft in the opposite direction to the third flexible thread to a position a selected distance from the second release wire;

o) engaging the fourth flexible thread into the graft material and/or a stent strut, and p) drawing the ends of the fourth thread together and tying ends of the thread, whereby the selected distance is reduced thereby reducing the overall diameter of the stent graft.

In an alternative form the invention comprises a temporary diameter reduction and constraint arrangement for a stent graft, the stent graft comprising a biocompatible graft material tube of a selected diameter and a plurality of self expanding stents fastened thereto, the stents comprising zig-zag stents comprising struts and bends therebetween, the temporary diameter reduction and constraint arrangement comprising two release wires extending longitudinally and helically in opposite directions along the graft material tube from substantially one side of the graft material tube at the first end of the graft material tube to substantially the opposite side of the graft material tube at the second end of the graft material tube, the release wires being stitched into the graft material tube, at a plurality of positions along each release wire two threads engaged around each release wire and a selected strut of a stent and portion of the stent graft circumferentially spaced a selected distance away from each release wire in each circumferential direction from the respective release wires and drawn tight to compress the self expanding stent between the selected strut and the release wire and tied to reduce the circumference and hence the overall diameter of the stent graft.

BRIEF DESCRIPTION OF THE DRAWING

This then generally describes the invention but to assist with understanding reference will now be made to drawings which show preferred embodiments of the invention.

In the drawings.

DETAILED DESCRIPTION

Now looking more closely at the drawings and in particular FIGS. 1A to F and FIG. 2 it will be seen that a stent graft 10 is a tubular body of a suitable graft material and has a proximal end 12 and a distal end 14. A scallop 13 is provided in the stent graft at the proximal end 12. The scallop would allow the stent graft to be deployed further around the thoracic arch of a patient thereby providing a larger landing zone for the stent graft without occluding the left subclavian artery. Stents on the stent graft are omitted in FIGS. 1 and 2 for the sake of clarity.

Figure 1A:
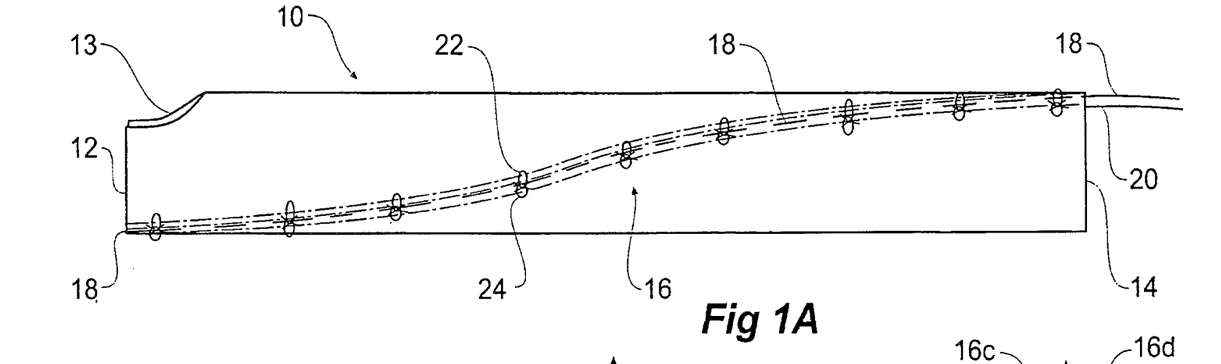
FIG. 1A shows a schematic view of a stent graft with a helical diameter reducing tie arrangement and stylised cross sectional views at various stages along the length of the stent graft according to one embodiment of the present invention.

The stent graft is schematically depicted in a diameter reduced state by the use of a diameter reducing arrangement generally shown as 16. The diameter reducing arrangement includes release wires 18 and 20 which extend down each side of the stent graft in a part helical manner in opposite directions from the distal end 14 to the proximal end 12. The release wire 18 is stitched in and out of the graft material along the length of the stent graft to maintain it in position. The release wire 20 is in a similar configuration on the other side of the stent graft. At intervals along the length of the stent graft threads 22 and 24 are looped around the release wire and extended in opposite circumferential directions as will be discussed in detail with reference to FIGS. 5A and 5B to hold the stent graft in a partially diameter reduced state. The diameter reducing arrangements on each side therefore extend in a part helical manner from one end of the stent graft to the other.

The cross sectional views FIGS. 1B to 1F at various stages along the length of the stent graft shown in FIG. 1A illustrate in a stylised manner how the diameter reducing ties 22, 24 progress circumferentially around the sides of the stent graft from one end to the other and are tied to the release wires 18 and 20.

Figures 1B, 1C, 1D:
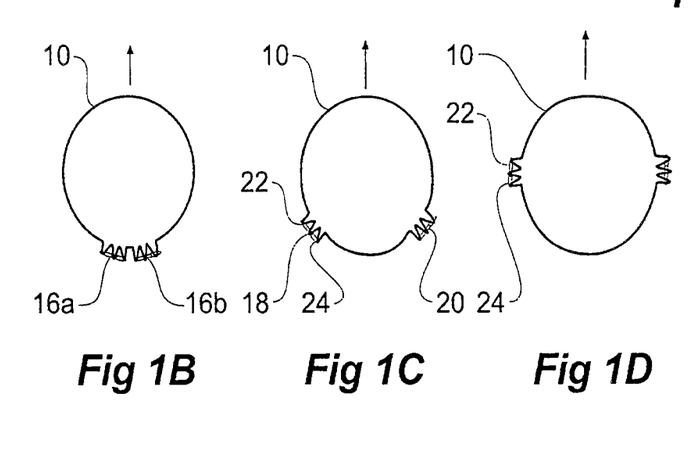
FIGS. 1B to 1F show schematic cross sections along the length of the stent graft shown in FIG. 1A.
Figure 1E:
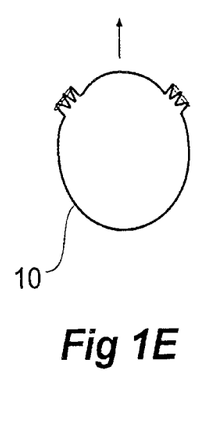
Figure 1F:
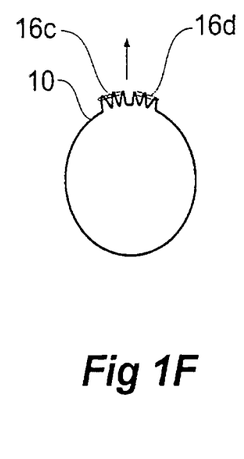

At the proximal end of the stent graft 12 as shown in FIG. 1B the regions of diameter reduction 16a and 16b are close to each other at one side of the stent graft. At the distal end of the stent 14 as shown in FIG. 1F the regions of diameter reduction 16c and 16d are close to each other at the other side of the stent graft. Between the proximal and distal ends as shown progressively in FIGS. 1C, 1D and 1E the regions of diameter reduction regions are positioned progressively up each side of the stent graft.

Figures 2, 6:
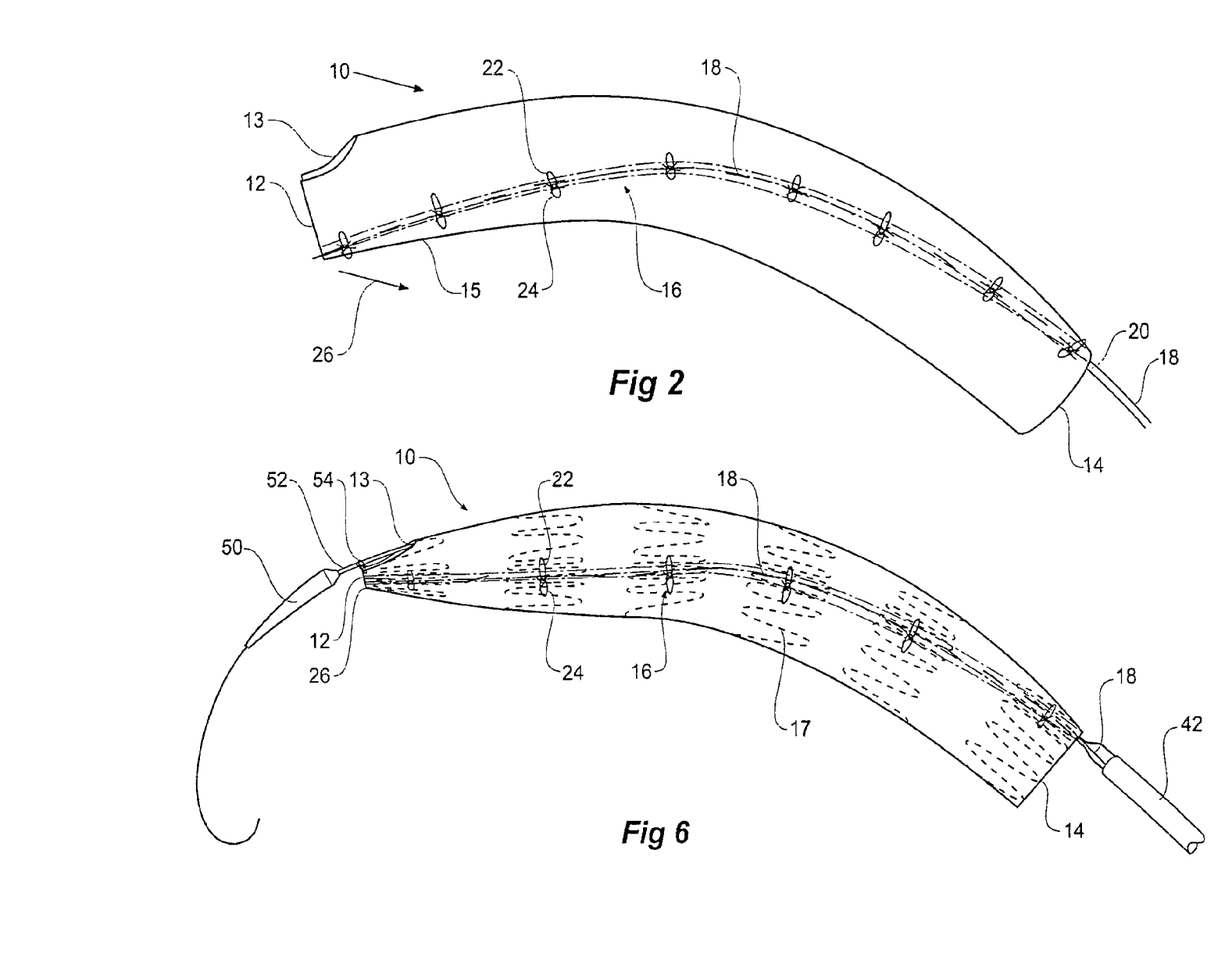
FIG. 2 shows a schematic view of the stent graft of FIG. 1 with the stent graft curved as it would be upon partial release within a curved lumen of the body.
FIG. 6 shows a schematic view of a stent graft with a diagonal or helical diameter reducing tie arrangement mounted onto a delivery device and including a proximal retention arrangement according to an alternative embodiment of the present invention.

FIG. 2 shows a schematic view of the stent graft 10 of FIG. 1 with the stent graft curved as it would be upon partial release within a curved lumen of the body. The deployment device upon which the stent graft is carried is not shown for purposes of clarity. When the release wires 18 and 20 are pulled to release the diameter reducing ties 22 and 24 then the friction between the release wires and the threads and the graft material will cause the inner curved side 15 of the end 12 to be pulled in a direction shown by the arrow 26 thereby encouraging the inner curved side 15 of the end 12 to correctly engage against the wall of a lumen as it is released from it's temporary diameter constraint.

Figure 3:
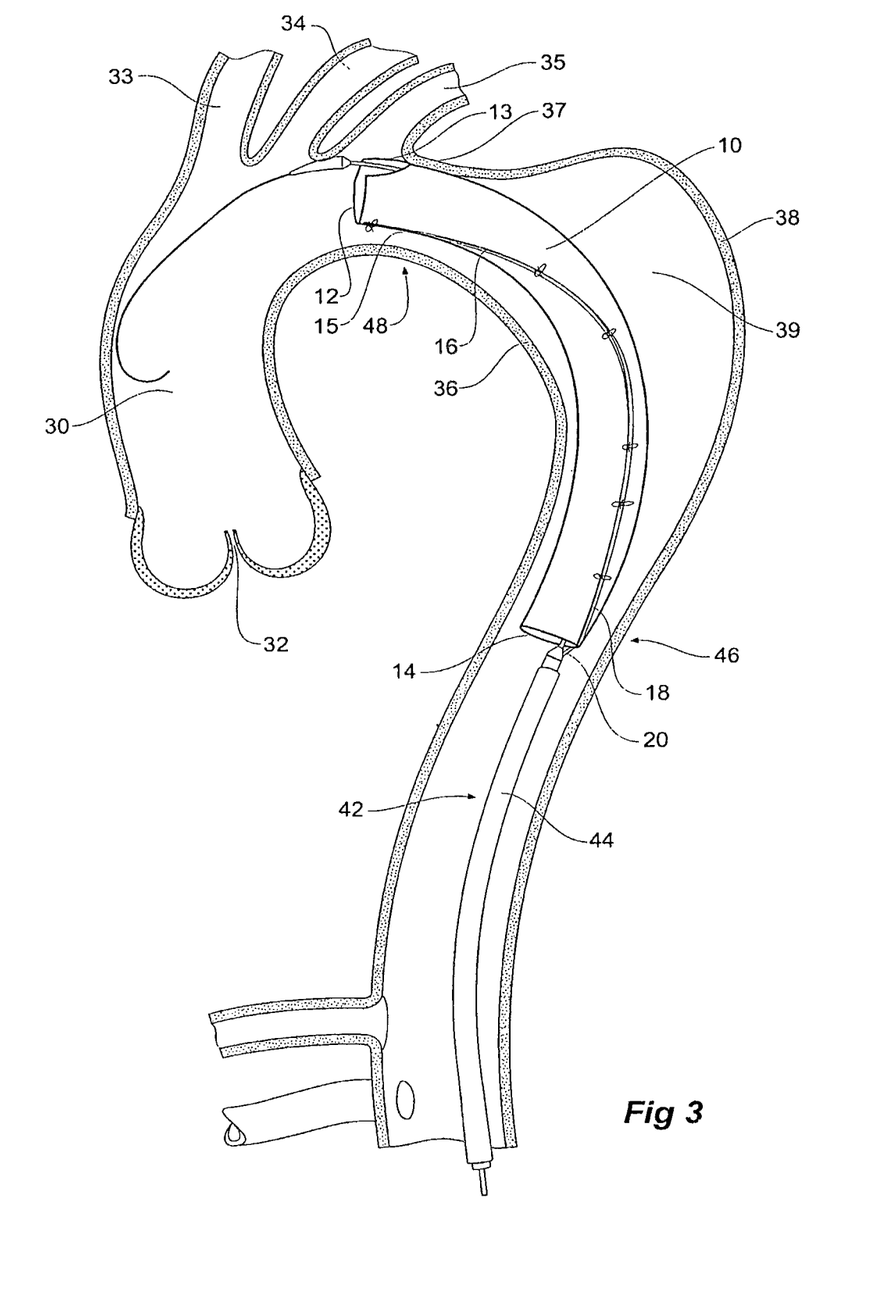
FIG. 3 shows a schematic view of the thoracic arch of the aorta of a patient with an aneurysm and with a stent graft at the partially released stage positioned in the aorta.
Figure 4:
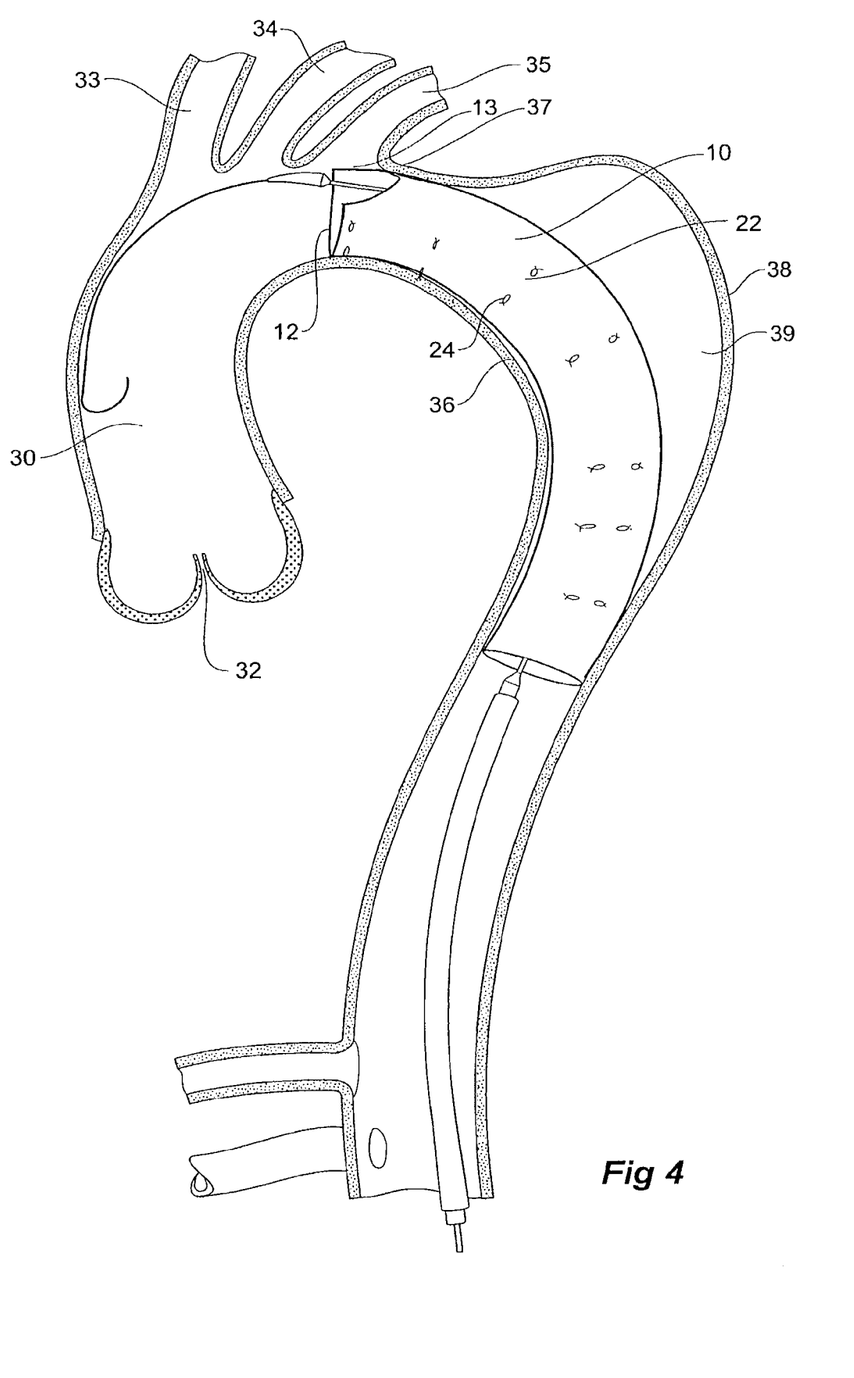
FIG. 4 shows the view of FIG. 3 with the diameter reducing ties withdrawn and the stent graft expanded to the walls of the thoracic arch.

FIG. 3 shows a schematic view of the thoracic arch of the aorta of a patient with an aneurysm and with a stent graft at the partially released stage positioned in the aorta and FIG. 4 shows the view of FIG. 3 with the diameter reducing ties withdrawn and the stent graft expanded to the walls of the thoracic arch.

The thoracic arch portion of the aorta comprises an ascending aorta 30 which receives blood from the heart (not shown) though an aortic valve 32. At the upper end of the ascending aorta there are branches for the innominate artery 33, the left common carotid artery 34 and the left subclavian artery 35. The aorta after these is referred to as the descending aorta 36 and it is in this region that an aortic aneurysm can occur. In an aortic aneurysm the wall of the aorta expands out to form a bulge 38 to leave an aneurysmal sac 39 which in serious cases can rupture with potentially fatal consequences. The aim of endovascular deployment of a stent graft is to isolate the aneurysmal sac by bypassing it with a stent graft. An important feature of placement of a stent graft in this region is that there is enough landing zone in the region 37 adjacent to the left subclavian artery 35 for the proximal end of the stent graft to adequately seal against a non-aneurysed portion of the thoracic arch. To ensure a sufficient landing zone the stent graft 10 can be provided with a scallop 13 which, when the stent graft is deployed will allow placement of the stent graft further up in the thoracic arch without occlusion of the subclavian artery 35.

As can be seen in FIG. 3 the stent graft has been introduced on a deployment device 42 and at the stage shown in FIG. 3 the sheath 44 has been withdrawn so that the stent graft 10 has partially expanded. At this stage the stent graft can still be moved on the introduction device to its desired position. The temporary diameter reducing arrangement 16 on the stent graft 10 extends from the outside of the curve 46 at the distal end 14 of the stent graft to the inside of the curve 48 at the proximal end 12 of the stent graft.

When the release wires 18 and 20 are retracted the stent graft expands to the wall of the vessel as is shown in FIG. 4. It will be noted that the diameter reducing threads 22 and 24 remain in the graft after removal of the release wires but as they are on the outside of the stent graft they do not occlude blood flow through the graft or provide points for formation of thromboses.

By having the diameter reducing ties in the part helical configuration from one end of the stent graft to the other there are a number of advantages. A first is that upon partial release the outer side of the curve at the proximal end expands more fully while at the same time still being maneuverable which allows the scallop 13 to be more opened and hence easier to visualise and position correctly. A second advantage is that when the diameter reducing ties are released by withdrawing the release wire they actually pull the inner curve side 15 of the proximal end 12 towards the inner curve of the lumen 48 thereby assisting the inner side of the proximal end of the stent graft 10 to correctly engage with the wall of the lumen. A further advantage is that when the stent graft 10 is in its curved and partially released configuration as shown in FIG. 3 the release wires 18 and 20 of the diameter reducing arrangement are substantially straighter between the ends 14 and 12 of the stent graft thereby reducing the chance that the release wire will buckle and be difficult to withdraw when required. At the distal end of the stent graft the delivery device tends to be positioned at the outside of the curve of the stent graft. The region at the distal end where the release wires 18 and 20 exit the stent graft is also on the outside of the curve of the stent graft and hence the wires can easily enter the delivery device 42 again reducing the chance that the release wire will buckle and be difficult to withdraw when required.

Figure 5A:
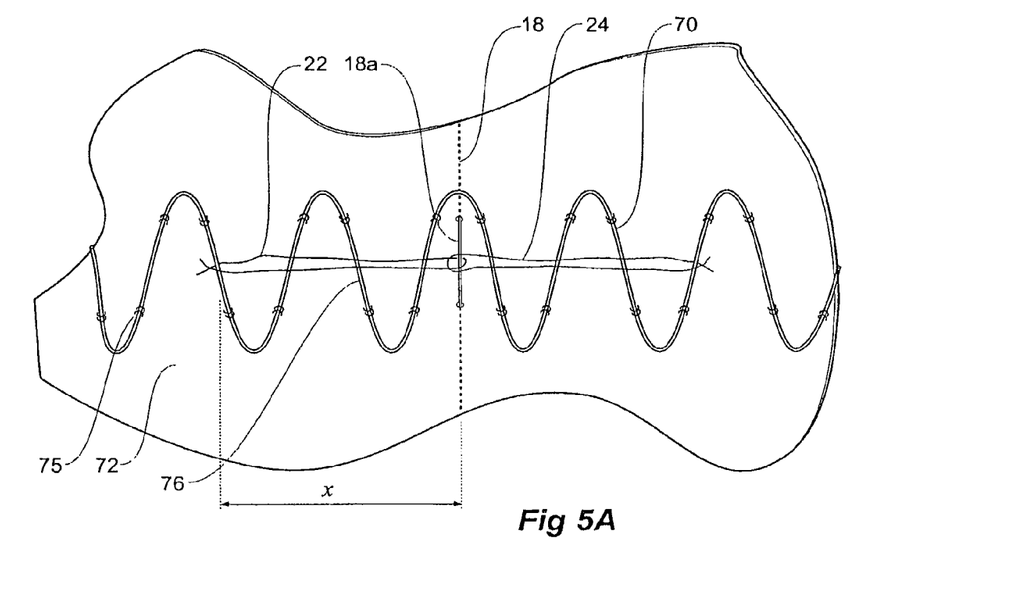
FIGS. 5A and 5B show detail of a diameter reducing arrangement useful for the present invention.
Figure 5B:
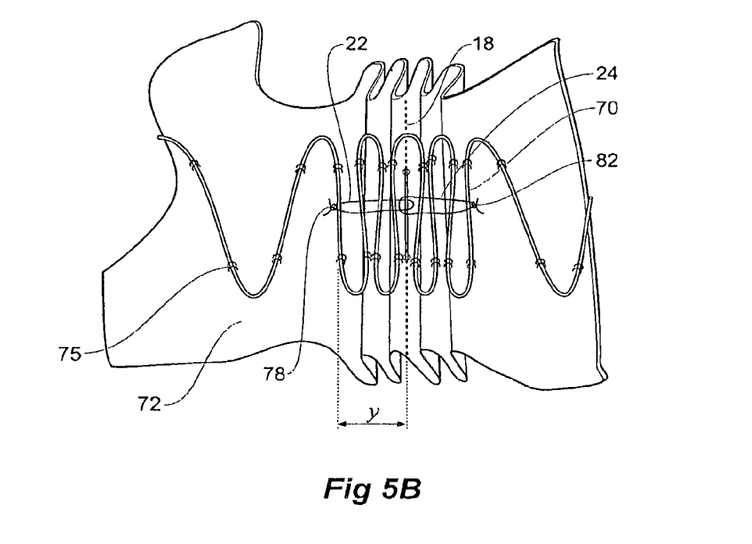

FIGS. 5A and 5B show schematically one embodiment of diameter reducing tie arrangement useful for the present invention. In this drawing only a portion of the graft material of a stent graft is shown and only a portion of a self expanding stent is shown fastened to it and stretched out flat.

As can be seen in FIG. 5A, a self expanding stent 70 which would extend around the tubular body of a stent graft and be stitched by stitches 75 to the graft material 72 of the stent graft is shown. A release wire 18 is stitched longitudinally along the graft material of the stent graft as was seen in FIG. 1 with a stitch 18a of the release wire being exposed to the outside of the stent graft in the region of the self expanding stent 70.

A first suture thread 22 of a flexible material is passed around the release wire 18 and extended out to one side of the release wire over the struts 76 of the stent graft to pass over two or three struts and to be looped around a third or fourth strut and into the graft material 72. The suture thread 22 is then pulled tight and knotted as shown in FIG. 5B with a knot 78 so that the struts between the release wire 18 and the knot 78 are pulled closer together against the resilient force of the self expanding stent 70.

A similar action is carried out to the other side of the release wire with a second suture thread 24 of a flexible material. In this case the thread 24 can either pass around the release wire 18 or be passed underneath the two strands of the thread 22 and over the release wire 18 and then it can be passed over two or three struts and then looped around a third or fourth strut and into the graft material 72 and pulled tight and knotted at 82.

The reduction in distance between the release wire 18 and the knot 78 may be from 50 to 75 percent. For instance if the distance x in FIG. 5A is 15 millimeters around the circumference of the stent graft from the release wire 18 to the strut at which the knot 78 is placed then this can be reduced to 5 millimeters as shown by the dimension y in FIG. 5B. With two diameter reducing ties, one to each side of the release wire 72, therefore a total circumference reduction of 20 millimeters can be achieved which will change the diameter of a 36 millimeter stent graft to approximately 28 millimeters. This can be less than the diameter of the aorta in that region into which the stent graft is deployed which means that the stent graft will still be maneuverable within the aorta while still mounted onto the deployment device but partially freed by the withdrawal of a containing sheath.

FIG. 6 shows a schematic view of a stent graft with a diagonal or helical diameter reducing tie arrangement mounted onto a delivery device and including a proximal retention arrangement according to an alternative embodiment of the present invention. The embodiment is similar to that shown in FIG. 1 and the same reference numerals are used for corresponding items.

In FIG. 6 it can be seen that a stent graft 10 has a proximal end 12 and a distal end 14. A scallop 13 is provided in the stent graft at the proximal end 12. The scallop would allow the stent graft to be deployed further around the thoracic arch of a patient to fit around the left subclavian artery, for instance, thereby providing a larger landing zone for the stent graft without occluding the left subclavian artery. Stent 17 on the stent graft is of the zig-zag or Z stent type and is shown dotted in FIG. 6 for the sake of clarity.

The stent graft is schematically depicted in a diameter reduced state by the use of a diameter reducing arrangement generally shown as 16. The diameter reducing arrangement includes release wires 18 extending down each side of the stent graft in a helical manner in opposite directions from a distal end 14 to the proximal end 12. The release wire 18 is stitched in and out of the graft material of the stent graft to maintain it in position. A further release wire is in a similar configuration on the other side of the stent graft. At intervals along the length of the stent graft threads 22 and 24 are looped around the release wire and extended in opposite circumferential directions as discussed in detail with reference to FIGS. 5A and 5B to hold the stent graft in a partially diameter reduced state. The diameter reducing arrangements on each side therefore extend in a part helical manner from one end of the stent graft to the other.

The stent graft is retained onto a delivery device 42 at its proximal end 12 just distal of a nose cone dilator 50 on a guide wire catheter 52 which passes through the stent graft 10. Retention is by fastening struts of the proximal most stent to a trigger wire (not shown) by means of a suture 54 as is explained in PCT Patent Publication WO 03/101518 entitled "Trigger Wire System for a Prosthesis Deployment Device" the teaching of which is incorporated herein in its entirety.

In this embodiment the diameter reducing ties at the proximal end 12 do not meet at the bottom of the graft but are positioned slightly up the respective sides of the graft and the distal end is held up to the guide wire catheter by the retention arrangement such that the proximal end of the stent graft is of a size which enables it to be positioned in the ascending aorta or the thoracic arch as necessary before final release.

Throughout this specification various indications have been given as to the scope of the invention but the invention is not limited to any one of these but may reside in two or more of these combined together. The examples are given for illustration only and not for limitation.

The invention claimed is:

1. A method of temporarily reducing the diameter of a stent graft at a plurality of positions along the stent graft, the stent graft comprising a tubular body of a biocompatible graft material and having a proximal end and a distal end and a self expanding stent framework extending from the proximal end to the distal end and supporting the graft material, the method comprising the steps of;
   a) extending at least one release wire longitudinally and in only a single half circumferential turn along the stent graft from substantially one side of the stent graft at the proximal end of the stent graft to substantially the opposite side of the stent graft at the distal end of the stent graft along the length of the stent graft;
   b) stitching the at least one release wire into the graft material;
   c) providing a plurality of diameter reducing segments at each of a plurality of positions along the length of the at least one release wire;
   d) engaging each of the plurality of diameter reducing segments around the at least one release wire and extending each of the plurality of diameter reducing segments at least partially about the circumference of the stent graft to a position a selected distance from the at least one release wire; and
   e) tightening each of the plurality of diameter reducing segments such that the selected distance is reduced and the overall diameter of the stent graft is reduced.

2. The method of claim 1, wherein the plurality of diameter reducing segments each comprise a first thread having ends, and the step of tightening comprises engaging the first thread into the graft material, drawing the ends of the first thread together and tying the ends of the first thread to reduce the overall diameter of the stent graft.

3. The method of claim 1 wherein the stent framework comprises a series of self expanding stents having struts and the step of engaging the threads into the graft material includes engaging the thread around a plurality of struts of the stent.

4. The method of claim 2, wherein each of the plurality of diameter reducing segments comprises a second thread, and the method further comprises the steps of
   f) passing the second thread around the at least one release wire, and
   g) extending the second thread at least partially about the circumference of the stent graft in the opposite direction to the first thread to a second position a selected second distance from the at least one release wire;
   h) engaging the second thread into the graft material, and
   i) tightening the second thread such that the second selected distance is reduced.

5. A method of temporarily reducing the diameter of a stent graft at a plurality of positions along the stent graft, the stent graft comprising a tubular body of a biocompatible graft material and having a proximal end and a distal end and a self expanding stent framework extending from the proximal end to the distal end and supporting the graft material, the method comprising the steps of;
   a) extending at least a first release wire longitudinally and in only a single half circumferential turn along the stent graft from substantially one side of the graft material tube at the proximal end of the graft material to substantially the opposite side of the graft material tube at the distal end of the graft material along the length of the stent graft;
   b) stitching the at least one release wire into the graft material;
   c) providing a plurality of diameter reducing segments at each of a plurality of positions along the release wire;
   d) engaging each of the plurality of diameter reducing segments around the at least one release wire and extending each of the plurality of diameter reducing segments at least partially about the circumference of the stent graft to a position a selected distance from the at least one release wire; and e) tightening each of the plurality of diameter reducing segments such that the selected distance is reduced and the overall diameter of the stent graft is reduced;
f) extending at least one second release wire longitudinally and in only a single half circumferential turn along the length of the stent graft from substantially one side of the stent graft at the proximal end of the stent graft opposite the first wire to substantially the opposite side of the stent graft at the distal end of the graft material opposite the first release wire;
g) stitching the at least one second release wire into the graft material;
h) providing a second plurality of diameter reducing segments at each of a plurality of positions along the at least one second release wire;
i) engaging each of the second plurality of diameter reducing segments around the at least one second release wire and extending each of the second plurality of diameter reducing segments at least partially about the circumference of the stent graft to a position a selected distance from the at least one second release wire in a direction opposite the first plurality of diameter reducing segments; and
j) tightening each of the second plurality of diameter reducing segments such that the selected distance is reduced and the overall diameter of the stent graft is further reduced.

6. The method of claim 5, wherein the first and second plurality of diameter reducing segments each comprise at least one thread having ends, and the step of tightening comprises engaging the at least one thread into the graft material, drawing the ends of the at least one thread together and tying the ends of the at least one thread.

7. The method of claim 5 wherein the stent framework comprises a series of self expanding stents having struts and the step of engaging the threads into the graft material includes engaging the threads around a plurality of struts of a stent.

* * * * *